United States Patent
Inoguchi et al.

(10) Patent No.: US 11,382,925 B2
(45) Date of Patent: Jul. 12, 2022

(54) AGENT FOR TREATING RETINAL DISEASE

(71) Applicant: CARNA HEALTH SUPPORT LTD., Fukuoka (JP)

(72) Inventors: Toyoshi Inoguchi, Fukuoka (JP); Mayumi Yamato, Fukuoka (JP)

(73) Assignee: CARNA HEALTH SUPPORT LTD., Fukuoka (JP)

( * ) Notice: Subject to any disclaimer, the term of this patent is extended or adjusted under 35 U.S.C. 154(b) by 114 days.

(21) Appl. No.: 16/761,664

(22) PCT Filed: Nov. 7, 2017

(86) PCT No.: PCT/JP2017/040017
§ 371 (c)(1),
(2) Date: May 5, 2020

(87) PCT Pub. No.: WO2019/092770
PCT Pub. Date: May 16, 2019

(65) Prior Publication Data
US 2021/0154218 A1    May 27, 2021

(51) Int. Cl.
*A61K 31/7042*    (2006.01)
*A61P 27/02*    (2006.01)

(52) U.S. Cl.
CPC .......... *A61K 31/7042* (2013.01); *A61P 27/02* (2018.01)

(58) Field of Classification Search
CPC .................................................. A61K 31/7042
See application file for complete search history.

(56) References Cited

U.S. PATENT DOCUMENTS

| | | |
|---|---|---|
| 2011/0065658 A1 | 3/2011 | Leslie |
| 2016/0113953 A1 | 4/2016 | Gannedahl et al. |
| 2018/0104268 A1 | 4/2018 | Mayoux et al. |
| 2019/0192482 A1 | 6/2019 | Minamino |
| 2019/0240243 A1 | 8/2019 | Inoguchi et al. |

FOREIGN PATENT DOCUMENTS

| | | |
|---|---|---|
| JP | 2011-520965 | 7/2011 |
| WO | 2018/037581 | 3/2018 |
| WO | 2018/043463 | 3/2018 |

OTHER PUBLICATIONS

Patel, Dhaval et al., Indian Journal of Clinical and Experimental Ophthalmology, "A study to determine association of serum uric acid level with age related macular degeneration", Apr.-Jun. 2017, vol. 3, No. 2, pp. 142-146 (Year: 2017).*
Sumino, Hiroyuki et al., The Lancet, "Reduction of serum uric acid by hormone replacement therapy in postmenopausal women with hyperuricaemia", 1999, vol. 354, p. 650 (Year: 1999).*
Office Action dated Oct. 1, 2020 in Japanese Patent Application No. 2019-193015 with English translation.
Office Action dated May 26, 2020 in Application No. 16/327,649, published as US 2019/0240243 A1.
Bailey, "Renal glucose reabsorption inhibitors to treat diabetes", Trends in Pharmacological Sciences, vol. 32, No. 2, Feb. 2011, pp. 63-71.
Zaccardi et al., "Efficacy and safety of sodium-glucose cotransporter-2 inhibitors in type 2 diabetes mellitus: systematic review and network meta-analysis", Diabetes, Obesity and Metabolism, Aug. 2016, vol. 18, pp. 783-794.
Takakura et al., "Effect of ipragliflozin, an SGLT2 inhibitor, on progression of diabetic microvascular complications in spontaneously diabetic Torii fatty rats", Life Sciences, Jan. 2016, vol. 147, pp. 125-131.
Takahashi et al., "Luseogliflozin(TS-071), a Novel, Potent and Selective SGLT2 Inhibitor, Prevents Diabetic Retinopathy in Rats", Diabetes, Jun. 2012, vol. 61, Issue Supplemental 1, p. A279, col. 1082-P.
Dziuba et al., "Modeling Macrovascular and Microvascular Outcomes of the SGLT-2 Inhibitor Dapagliflozin vs. Standard of Care in Second-Line Diabetes Therapy", Diabetes, Jul. 2013, vol. 62, Issue Supplement 1, 2013, p. A672, col. 2641-P0.
Morsal et al., "Potential role of uric acid in the molecular pathogenesis of age-relate macular degenration", Medical Hypotheses, 2006, vol. 66, 793-796.
International Search Report in English issued in PCT/JP2017/040017, dated Jan. 30, 2018.

* cited by examiner

*Primary Examiner* — Bahar Craigo
(74) *Attorney, Agent, or Firm* — Greenblum & Bernstein, P.L.C.

(57) ABSTRACT

Agent for treating retinal disease such as aged-related maculopathy comprising sodium/glucose cotransporter2 inhibitor (SGLT2 inhibitor) as an active ingredient.

16 Claims, 2 Drawing Sheets

[Figure 1]
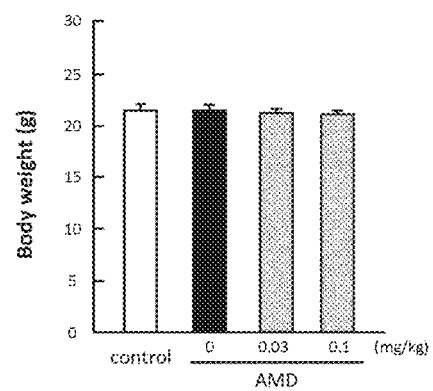
[Figure 2]
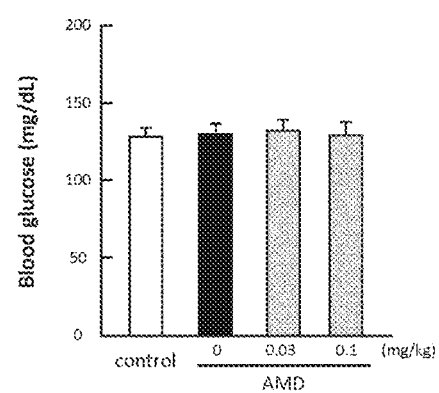

[Figure 3]
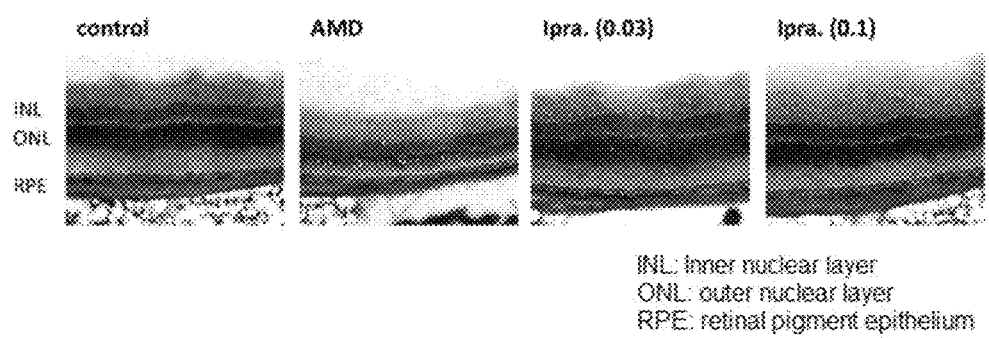
INL: inner nuclear layer
ONL: outer nuclear layer
RPE: retinal pigment epithelium
[Figure 4]
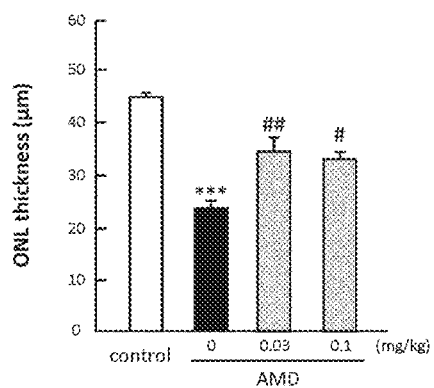

AGENT FOR TREATING RETINAL DISEASE

TECHNICAL FIELD

The present invention relates to an agent for treating retinal diseases.

BACKGROUND ART

Aged-related maculopathy which is one of retinal disease is the first causative disease of acquired blindness in adult in Europe and USA, and the fourth in Japan. Hereafter, due to the progression of the society's aging, it is thought the number of patients having aged-related maculopathy would increase around the world. Decrease of vision caused by this disease is the cause that significantly decreases the QOL of many patients. However, there is no effective treatment method at the moment.

Further, no oral therapeutic agent that suppresses or ameliorates progression or exacerbation of aged-related maculopathy, and the development is strongly awaited.

On the other hand, SGLT2 inhibitor agent is a therapeutic agent for diabetes that inhibits sodium/glucose co-transporter2 (SGLT2) that is specifically present in proximal renal tubules and performs reabsorption of glucose, and promotes glucose excretion from urine to show an antihyperglycemic action. Clinical application of six types of SGLT2 inhibitor agent has already been performed (see for example, non-patent documents 1, 2). However, it is not known that the SGLT2 inhibitor agent has a direct ameliorating effect on retinal diseases that is not cause by high blood sugar such as aged-related maculopathy.

PRIOR ART DOCUMENTS

Non-Patent Documents

Non Patent Document 1:
Bailey C J. Renal glucose reabsorption inhibitors to treat diabetes. Trends Pharmacil Sci 2011; 32:63-71
Non Patent Document 2:
Zaccadi F, Webb D R, Htike Z Z, Youssef D, Khunti K, Davies M J. Efficacy and safety of sodium-glucose co-transporter-2 inhibitors in type 2 diabetes mellitus: systematic review and network meta-analysis. Diab Obes Metab 2016; 18:783-94

SUMMARY OF THE INVENTION

Object to be Solved by the Invention

The object of the present invention is to provide an agent for treating and/or ameliorating retinal diseases such as aged-related maculopathy.

Means to Solve the Object

The present inventors made a keen study on action effect of SGLT2 inhibitor agent as a therapeutic agent for diabetes showing antihyperglycemic action. First, the present inventors focused that with respect to the actual administration amount of SGLT2 inhibitor agent, only a tiny amount reaches the proximal renal tubules where the SGLT2 inhibitor agent acts, and then found out that the existing SGLT2 inhibitor agent has an effect of ameliorating retinopathy caused by glucose (retinopathy caused by high blood sugar), with an administration amount that shows an antihyperglycemic action, and with a low dosage administration which does not show an antihyperglycemic action (PCT/JP2016/86658).

The present inventors further advanced their studies, and found out that SGLT2 inhibitor agent shows a protecting effect in aged-related maculopathy mouse model that does not show high blood sugar. Specifically, it has been found out that SGLT2 inhibitor agent exerts an ameliorating effect with a mechanism of suppressing sodium and/or glucose intake even on aged-related maculopathy which is a completely different disease (retinal disease that is not caused by high blood sugar) that is not caused by an excessive inflow of glucose in retinal constituting cells by high blood sugar. The present invention has been thus completed.

Specifically, the present invention relates to the following.
[1] An agent for treating retinal disease not caused by high blood sugar, comprising sodium/glucose co-transporter2 inhibitor (SGLT2 inhibitor) as an active ingredient.
[2] The agent for treating according to [1], which is administered at a low dosage whereby no lowering in blood sugar is observed.
[3] The agent for treating according to [1] or [2], wherein the SGLT2 inhibitor is at least one selected from canagliflozin, ipragliflozin, dapagliflozin, luseogliflozin, empagliflozin and tofogliflozin.
[4] The agent for treating according to any one of [1] to [3], wherein the retinal disease not caused by high blood sugar is aged-related maculopathy.

Effect of the Invention

According to the therapeutic agent of the present invention, retinal diseases that are not caused by high blood sugar such as age-related maculopathy can be treated by administering SGLT2 inhibitor agent at an administration amount whereby lowering in blood sugar is observed, and also with a lower dosage whereby no antihyperglycemic action is observed. As the therapeutic agent of the present invention exerts an effect with an administration at a low dosage, there is no problem of hypoglycemia, excessive urination/frequent urination, anhydration, urinary tract infection/genital infection, and increase of ketone body, which are main side effects caused by action of promoting urine sugar elimination of the existing SGLT2 inhibitor agents, and the safety is significantly high. The therapeutic agent of the present invention enables to expand a new application as a therapeutic agent for age-related maculopathy, etc.

BRIEF EXPLANATION OF DRAWINGS

FIG. 1 is a graph showing the effect of Ipragliflozin administration on the body weight of an age-related maculopathy mouse model. "Control" shows control mouse (n=9), and "AMD" shows an age-related maculopathy mouse model bred for one week after light irradiation (8000 lux, 10 hours). "0" shows AMD mouse (n=9) not administered with Ipragliflozin, and "0.03" shows AMD mouse (n=9) administered with 0.03 mg/kg/day of Ipragliflozin. "0.1" shows AMD mouse (n=9) administered with 0.1 mg/kg/day of Ipragliflozin.

FIG. 2 is a graph showing the effect of Ipragliflozin administration on the blood sugar of an age-related maculopathy mouse model. "Control" shows control mouse (n=9), and "AMD" shows an age-related maculopathy mouse model bred for one week after light irradiation (8000 lux, 10 hours). "0" shows AMD mouse (n=9) not administered with Ipragliflozin, and "0.03" shows AMD mouse (n=9) administered with 0.03 mg/kg/day of Ipragliflozin. "0.1" shows AMD mouse (n=9) administered with 0.1 mg/kg/day of Ipragliflozin.

FIG. 3 is a set of photographs showing Hematoxylin-Eosin staining of retina of an age-related maculopathy mouse model. "Control" shows control mouse, and "AMD" shows an age-related maculopathy mouse model bred for one week after light irradiation (8000 lux, 10 hours). "Ipra. (0.03)" shows AMD mouse administered with 0.03 mg/kg/day of Ipragliflozin, and "Ipra. (0.1)" shows AMD mouse administered with 0.1 mg/kg/day of Ipragliflozin.

FIG. 4 is a graph showing the thickness of outer granular layer (including visual cells) of the retina of an age-related maculopathy mouse model in numeral terms. "Control" shows control mouse (n=3), and "AMD" shows an age-related maculopathy mouse model (n=3) bred for one week after light irradiation (8000 lux, 10 hours). "0" shows AMD mouse (n=3) not administered with Ipragliflozin, and "0.03" shows AMD mouse (n=3) administered with 0.03 mg/kg/day of Ipragliflozin. "0.1" shows AMD mouse (n=3) administered with 0.1 mg/kg/day of Ipragliflozin. "***" represents P<0.005 vs control mouse, "#" and "##" each represents P<0.05 vs Ipragliflozin non-administered AMD mouse, and P<0.01 vs Ipragliflozin non-administered AMD mouse, respectively.

MODE OF CARRYING OUT THE INVENTION

The therapeutic agent of the present invention is an agent for treating retinal disease not caused by high blood sugar, and comprises an SGLT2 inhibitor as an active ingredient.

The present invention has found out that the SGLT2 inhibitor has an action of protecting retina, with a mechanism completely different from proximal tubule SGLT suppression, with an administration amount whereby lowering in blood sugar is observed, and in a lower dosage whereby no antihyperglycemic action is observed. Specifically, the present invention has found out that the SGLT2 inhibitor shows protection of retina function (action of protecting visual function) when the SGLT2 inhibitor suppresses intake of sodium and/or glucose in retinal constituting cells.

According to the therapeutic agent of the present invention, it is thought to suppress intake of sodium and/or glucose in retinal constituting cells, even in retinal disorders not caused by high blood sugar to ameliorate retinal functions. Actually, the SGLT2 inhibitor shows effects of ameliorating lesions in retina of an age-related maculopathy mouse model.

The retinal disease being the subject of the therapeutic agent of the present invention is not particularly limited as long as it is a retinal disease not caused by high blood sugar. For example, diseases by which a lesion occurs in retina by some reasons, and thereby the visual field is narrowed, or the vision is decreased can be exemplified. Specific examples include age-related maculopathy by which a lesion occurs in the macula which is the central part of retina with age, and retinitis pigmentosa, etc.

The SGLT2 inhibitor in the therapeutic agent of the present invention is not particularly limited as long as it binds to SGLT2 and shows an antagonistic inhibitory effect to intake of sodium and/or glucose via SGLT2.

Examples of SGLT2 inhibitors include canagliflozin, ipragliflozin, dapagliflozin, luseogliflozin, empagliflozin, tofogliflozin, etc. Specific examples include canagliflozin hydrate ($C_{24}H_{25}FO_5S.\frac{1}{2}H_2O$), ipragliflozin L-proline ($C_{21}H_{21}FO_5S.C_5H_9NO_2$), dapagliflozin propylene glycol hydrate ($C_{21}H_{25}ClO_6.C_3H_8O_2.H_2O$), luseogliflozin hydrate ($C_{23}H_{30}O_6S.xH_2O$), empagliflozin ($C_{23}H_{21}ClO_7$), tofogliflozin hydrate ($C_{22}H_{26}O_6.H_2O$), etc., which are active ingredients of existing SGLT2 inhibitor agents.

As in the above, in the present invention, for example the term "canagliflozin" relates to a compound having the following canagliflozin structure, and includes a pharmaceutical acceptable hydrate, alcohol adduct, amino acid adduct, etc. It is the same for other SGLT2 inhibitors such as "ipragliflozin", etc.

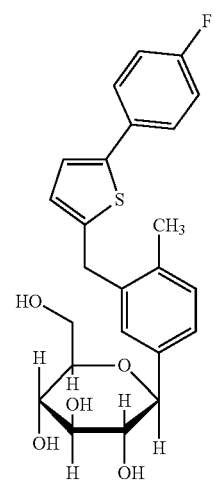

The administration amount of the therapeutic agent of the present invention can be an administration amount whereby lowering in blood sugar is observed, or it can be a lower dosage whereby no antihyperglycemic action is observed. Specifically, the therapeutic agent of the present invention acts by protecting retinal function by reaching an effective concentration that inhibits SGLT2 of retinal constituting cells such as visual cells in blood or in retinal tissues even by being administered at a low dosage that does not reach an effective concentration in urine for SGLT2 suppression.

The low dosage whereby no antihyperglycemic action is observed in the present invention is an amount by which blood sugar does not significantly decrease, and for example, in case of active ingredients of hypoglycemic agent in which SGLT2 inhibitor is authorized, it means a dosage lower than the authorized minimum dosage amount. The lower limit can be appropriately determined within the range with which an effect is exerted, and for example, for canagliflozin hydrate, it is approximately $\frac{1}{100}$ of the authorized minimum dosage amount. For ipragliflozin L-proline, the maximum blood concentration (Cmax) in the minimum dosage amount is similar with that of canagliflozin, and as the $IC_{50}$ level showing the inhibition activity is also similar, it is similarly approximately $\frac{1}{100}$ of the authorized minimum dosage amount.

In case of dapagliflozin propylene glycol hydrate, luseogliflozin hydrate, empagliflozin, tofogliflozin hydrates, as the maximum blood concentration (Cmax) in the minimum dosage amount is approximately $\frac{1}{10}$ of that of canagliflozin, while the $IC_{50}$ level is similar, it is approximately $\frac{1}{10}$.

Specifically, for canagliflozin hydrate which is authorized as a hypoglycemic agent, it is less than 100 mg per day for an adult (as canagliflozin), and it can be 90 mg or less, 70 mg or less, 50 mg or less, 30 mg or less, 10 mg or less, 5 mg or less, and the lower limit is approximately 1 mg.

For ipragliflozin L-proline, it is less than 50 mg per day for an adult (as ipragliflozin), and it can be 40 mg or less, 30 mg or less, 20 mg or less, 10 mg or less, 5 mg or less, 1 mg or less, and the lower limit is approximately 0.5 mg.

For dapagliflozin propylene glycol hydrate, it is less than 5 mg per day for an adult (as dapagliflozin), and it can be 4 mg or less, 3 mg or less, 2 mg or less, 1 mg or less, and the lower limit is approximately 0.5 mg.

For luseogliflozin hydrate, it is less than 2.5 mg per day for an adult (as luseogliflozin), and it can be 2 mg or less, 1.5 mg or less, 1 mg or less, 0.5 mg or less, and the lower limit is approximately 0.25 mg.

For empagliflozin, it is less than 10 mg per day for an adult, and it can be 9 mg or less, 6 mg or less, 4 mg or less, 2 mg or less, and the lower limit is approximately 0.1 mg.

For tofogliflozin hydrate, it is less than 20 mg per day for an adult (as tofogliflozin), and it can be 18 mg or less, 15 mg or less, 10 mg or less, 5 mg or less, and the lower limit is approximately 2 mg.

The dosage form of the therapeutic agent of the present invention includes a dosage form for oral administration, and for injection, etc., while it is preferred to be oral administration, similar as the existing SGLT2 inhibitor agent (hypoglycemic agent). Further, the form of the therapeutic agent of the present invention include various forms such as tablets, granules, powder, capsules, and liquid.

Further, as a method for treating retinal diseases not caused by high blood sugar using the therapeutic agent of the present invention, it is not particularly limited as long as it is a method of administrating the therapeutic agent of the present invention comprising SGLT2 inhibitor as an active ingredient to a patient at a dosage whereby lowering in blood sugar is observed or at a dosage whereby no lowering in blood sugar is observed. As it is stated in the above, examples of the administration method include oral administration, administration by injection, etc. The details of the therapeutic agent of the present invention and its administration amount, and specific examples of retinal diseases being the subject of treatment, etc. are as stated in the above.

EXAMPLE

[Preliminary Test]

To BALB/c mice, light irradiation (8000 lux, 10 hours) was performed, and then the mice were bred for one week. The existing SGLT2 inhibitor agent ipragliflozin was orally administered in an amount of 0.03 mg/kg/day and 0.1 mg/kg/day for four days including the day of light irradiation. The effects on body weight and blood sugar were confirmed. These models are widely used as age-related maculopathy models.

FIGS. 1 and 2 show the results of body weight and blood sugar levels when administering the existing SGLT2 inhibitor agent ipragliflozin at 0.03 mg/kg/day and 0.1 mg/kg/day.

As it is shown in FIG. 1 and FIG. 2, no change was observed in body weight and in blood sugar as compared to when not administering ipragliflozin, in either administration amount. As for urinal sugar, similarly as for body weight and blood sugar, no change was observed as compared to when not administering ipragliflozin.

Example 1

By Hematoxylin-Eosin staining, protecting effect was confirmed in retina at a low dosage (0.03 mg/kg/day, and 0.1 mg/kg/day) whereby no lowering in blood sugar was observed with ipragliflozin. The results are shown in FIG. 3 and FIG. 4. FIG. 4 shows a graph showing the numerical values of the measurement of thickness of outer granular layer (including visual cells) of retina.

As it is shown in FIG. 2, 0.03 mg/kg/day and 0.1 mg/kg/day of ipragliflozin are administration amounts not showing lowering in blood sugar. However, as it is shown in FIG. 3 and FIG. 4, by administering the amount of 0.03 mg/kg/day and 0.1 mg/kg/day of ipragliflozin, thinning of membrane shown in retina of AMD mouse was significantly ameliorated. In human age-related maculopathy, particularly in atrophic form, retinal pigment epithelium gradually becomes atrophic, retina is impaired and the vision is gradually decreased. Therefore, by the protection effect of retina by ipragliflozin, ultimately, amelioration of visual function can be expected.

As it is stated in the above, it has been apparent that the therapeutic agent of the present invention exerts an effect of ameliorating age-related maculopathy with a dosage whereby no lowering in blood sugar is observed.

INDUSTRIAL APPLICABILITY

The therapeutic agent of the present invention enables an enlargement of new application as a therapeutic agent for age-related maculopathy, etc. and industrial applicability is high.

The invention claimed is:

1. A method for treating retinal disease not caused by high blood sugar, comprising administering to a patient in need thereof a composition containing a therapeutically effective amount of sodium/glucose co-transporter2 inhibitor (SGLT2 inhibitor) as an active ingredient.

2. The method according to claim 1, wherein the SGLT2 inhibitor is administered at a dosage so that no lowering in blood sugar is observed upon administration.

3. The method according to claim 1, wherein the SGLT2 inhibitor is at least one selected from canagliflozin, ipragliflozin, dapagliflozin, luseogliflozin, empagliflozin and tofogliflozin.

4. The method according to claim 1, wherein the retinal disease not caused by high blood sugar is aged-related maculopathy.

5. The method according to claim 2, wherein the SGLT2 inhibitor is at least one selected from canagliflozin, ipragliflozin dapagliflozin, luseogliflozin, empagliflozin and tofogliflozin.

6. The method according to claim 2, wherein the retinal disease not caused by high blood sugar is aged-related maculopathy.

7. The method according to claim 3, wherein the retinal disease not caused by high blood sugar is aged-related maculopathy.

8. The method according to claim 1, wherein the SGLT2 inhibitor comprises at least one of, as canagliflozin, at a therapeutic dose of less than 100 mg per day; as ipragliflozin, at a therapeutic dose of less than 50 mg per day; as dapagliflozin, at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

9. The method according to claim 2, wherein the SGLT2 inhibitor comprises at least one of, as canagliflozin, at a therapeutic dose of less than 100 mg per day; as ipragliflozin, at a therapeutic dose of less than 50 mg per day; as dapagliflozin, at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

10. The method according to claim 3, wherein the SGLT2 inhibitor comprises at least one of, as canagliflozin, at a therapeutic dose of less than 100 mg per day; as ipragliflozin, at a therapeutic dose of less than 50 mg per day; as dapagliflozin, at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

11. The method according to claim 4, wherein the SGLT2 inhibitor comprises at least one of, as canagliflozin, at a therapeutic dose of less than 100 mg per day; as ipragliflozin, at a therapeutic dose of less than 50 mg per day; as dapagliflozin, at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

12. A method for treating a patient having retinal disease not caused by high blood sugar, comprising administering to the patient a composition containing sodium/glucose co-transporter2 inhibitor (SGLT2 inhibitor) as an active ingredient.

13. The method according to claim 12, comprising administering to the patient a composition containing sodium/glucose co-transporter2 inhibitor (SGLT2 inhibitor) as an active ingredient, to therapeutically treat retinopathy not caused by high blood sugar without showing an antihyperglycemic action.

14. The method according to claim 12, wherein the SGLT2 inhibitor is at least one selected from canagliflozin, ipragliflozin, dapagliflozin, luseogliflozin, empagliflozin and tofogliflozin.

15. The method according to claim 12, wherein the retinal disease not caused by high blood sugar is aged-related maculopathy.

16. The method according to claim 12; wherein the SGLT2 inhibitor comprises at least one of, as canagliflozin, at a therapeutic dose of less than 100 mg per day; as ipragliflozin, at a therapeutic dose of less than 50 mg per day; as dapagliflozin; at a therapeutic dose of less than 5 mg per day; as luseogliflozin, at a therapeutic dose of less than 2.5 mg per day; as empagliflozin, at a therapeutic dose of less than 10 mg per day; and, as tofogliflozin, at a therapeutic dose of less than 20 mg per day.

* * * * *